United States Patent [19]
Mokry

[11] Patent Number: 5,032,121
[45] Date of Patent: * Jul. 16, 1991

[54] ABSORBENT ARTICLE HAVING A CUP-SHAPED CONFIGURATION

[75] Inventor: Patti J. Mokry, Auburn, Wash.

[73] Assignee: Kimberly-Clark Corporation, Neenah, Wis.

[*] Notice: The portion of the term of this patent subsequent to Jul. 31, 2007 has been disclaimed.

[21] Appl. No.: 521,857

[22] Filed: May 8, 1990

Related U.S. Application Data

[63] Continuation-in-part of Ser. No. 843,332, Mar. 24, 1986, Pat. No. 4,944,735, which is a continuation of Ser. No. 581,945, Feb. 21, 1984, abandoned.

[51] Int. Cl.$^5$ .............................................. A61F 13/16
[52] U.S. Cl. ................................ 604/385.2; 604/366
[58] Field of Search ................. 604/385.2, 366, 385.1, 604/370

[56] References Cited

U.S. PATENT DOCUMENTS

| | | | |
|---|---|---|---|
| 3,371,668 | 3/1968 | Johnson | 128/290 |
| 3,639,917 | 2/1972 | Althouse | 2/270 |
| 3,805,790 | 4/1974 | Kaczmarzyk et al. | 128/290 |
| 3,819,401 | 6/1974 | Massengale et al. | 156/85 |
| 3,848,599 | 11/1974 | Schaar | 128/287 |
| 3,860,003 | 1/1975 | Buell | 128/287 |
| 3,912,565 | 10/1975 | Koch et al. | 156/85 |
| 4,226,238 | 10/1980 | Bianco | 128/287 |
| 4,259,220 | 3/1981 | Bunnelle et al. | 260/27 |
| 4,261,782 | 4/1981 | Teed | 156/361 |
| 4,309,236 | 1/1982 | Teed | 156/164 |
| 4,324,245 | 4/1982 | Mesek et al. | 128/287 |
| 4,324,246 | 4/1982 | Mullane et al. | 128/287 |
| 4,326,528 | 4/1982 | Ryan et al. | 128/287 |
| 4,337,771 | 7/1982 | Pieniak et al. | 128/287 |
| 4,352,355 | 10/1982 | Mesek et al. | 128/287 |
| 4,357,938 | 11/1982 | Ito et al. | 128/287 |
| 4,490,147 | 12/1984 | Pierce et al. | 604/378 |
| 4,490,148 | 12/1984 | Beckestrom | 604/385 |
| 4,496,360 | 1/1985 | Joffe et al. | 604/397 |
| 4,579,556 | 4/1986 | McFarland | 604/385 |
| 4,668,230 | 5/1987 | Damico et al. | 604/385 |
| 4,701,177 | 10/1987 | Ellis et al. | 604/385 |
| 4,770,657 | 9/1988 | Ellis et al. | 604/385 |
| 4,944,735 | 7/1990 | Mokry | 604/385.1 |

FOREIGN PATENT DOCUMENTS 0091412  10/1983  European Pat. Off.

Primary Examiner—C. Fred Rosenbaum
Assistant Examiner—Sharon Finkel
Attorney, Agent, or Firm—Thomas J. Connelly

[57] ABSTRACT

An absorbent article is disclosed which has a cup-shaped configuration which prevents side leakage of body fluid and better conforms to the curve shape of a human torso. The absorbent article includes an absorbent having a first surface which faces the body of a user and a second surface aligned opposite to the first surface. The absorbent has a pair of longitudinally extending arcuate sides which are arranged to be close to each other at a point approximate a central portion of the absorbent. A fluid permeable cover is positioned adjacent to at least the first surface of the absorbent and a fluid-impermeable baffle is positioned adjacent to at least the second surface of the absorbent. The cover and baffle are sealed together to enclose the absorbent. The seal is formed inward of the outer peripheral edge of the article. The article further includes a pair of elastic members affixed between the cover and the baffle, outward of the seal and aligned adjacent to the central portion of the absorbent. The elastic members cause the absorbent article to acquire a cup-shaped configuration which corresponds to the perineal area of a user.

17 Claims, 2 Drawing Sheets

ABSORBENT ARTICLE HAVING A CUP-SHAPED CONFIGURATION

This application is a continuation-in-part of U.S. Ser. No. 06/843,332 filed March 24, 1986 now U.S. Pat. No. 4,944,735 which in turn is a continuation application of U.S. Ser. No. 581,945 filed Feb. 21, 1984, now abandoned.

FIELD OF THE INVENTION

This invention relates to an absorbent article, especially to sanitary napkins and pantiliners, wherein the article has a cup-shaped configuration which prevents side leakage and better conforms to the shape of the human body.

BACKGROUND OF THE INVENTION

Most absorbent articles, especially feminine pads, sanitary napkins, pantiliners, incontinent garments and the like, which are manufactured today are long and narrow and usually are relatively flat. These flat products are designed to be worn tightly against the curved torso of a human body and are generally held in place by an undergarment. Such flat products have a tendency to buckle or wrinkle as they conform to the body profile as the undergarment is pulled up and secured around the wearer's torso. These buckles and wrinkles can facilitate side leakage of body fluids which have been deposited onto the cover of the product. Side leakage is probably the number one reason way these types of absorbent articles fail.

In most instances, fluid leakage results not from saturation of the absorbent material but rather from fluid running off of the cover material. It is common for body fluid deposited onto the cover to form a pool before it penetrates down through the fluid permeable cover and into the absorbent. This pooling effect is due to a variety of factors, such as the size openings in the cover, the fluid permeability of the cover material, the amount of fluid discharged onto the cover in a short period of time, as well as the composition of the fluid itself. Body fluid may contain menses, blood, urine and other aqueous fluids. Menses, in particular, is a complex fluid which may be highly viscous and normally contains a mucoidal fraction, as well as cellular debris, amongst other aqueous components. Both the mucoidal fraction and the cellular debris tend to collect at the surface capillaries of the cover material and block the passage of the more aqueous components into the absorbent.

Side leakage occurs when the deposited body fluid pools on the cover material and is allowed to spread along the surface of the cover before being absorbed into the absorbent. Body movement and wrinkles in the product commonly assist the fluid in flowing outwardly. Since the side edges are closer to the fluid discharge area then are the distal ends, the product tends to leak at the side edges rather than at the ends. Such side leakage usually occurs well before the bulk of the absorbent has been wetted or insulted.

Attempts have been made to increase comfort of feminine care products as well as to insure greater surface contact in the perineal area by providing products having an hourglass shape. U.S. Pat. Nos. 3,805,790 and 4,490,147 teach two different hourglass shapes. An hourglass shaped product conforms better to the shape of the human thighs, especially adjacent to the perineal area. U.S. Pat. No. 4,324,246 shows an absorbent article with a seam formed inward of the outer peripheral edge along with a narrow central portion to provide a better fit with the body. A better fit means less distortion during body movement and should create a better interface between the perineal area and the cover.

Various attempts at producing a feminine product with side flaps or walls have also been tried. Examples include EPA 0,091,412 which teaches a sanitary napkin which utilizes a thicker and wider absorbent in the central portion but which also uses elastic to form upstanding walls. U.S. Pat. Nos. 4,579,556 and 4,668,230 teach arcuate shaped products having a rectangular absorbent and elastic secured to either a portion of or along the entire length of the longitudinal edges. The elastic forms upstanding walls which assist in preventing side leakage of body fluid. Two additional U.S. Pat. Nos. 4,701,177 and 4,770,657 teach three-dimensional shaped feminine pads having elasticized edges and an overall concave shape to better fit the female body. These last two patents are assigned to the present assignee and were filed after the date of the parent case to which this application depends.

Diapers represent another type of absorbent article which have experimented with leg elastics. Several U.S. Pat. Nos. which teach the use of elastic to form a body seal include: 3,860,003; 4,324,245; 4,326,528; 4,337,771; 4,352,355 and 4,496,360. It should be noted that diapers are different from feminine care products in that they do not require the same intimate contact between the wearer's body and the product itself. However, the use of elastic to form side seals is relevant to both types of products.

Now an absorbent article has been developed which has a cup-shaped configuration so as to prevent side leakage of body fluid and better conform to the curve shape of a human torso.

SUMMARY OF THE INVENTION

Briefly, this invention relates to an absorbent article, such as a feminine pad, sanitary napkin, pantiliner, light incontinent device, etc., which has a cup-shaped configuration. The absorbent article is designed to form a better fit with the human torso and the cup-shaped configuration includes upstanding side walls which prevent side leakage of body fluids deposited onto the cover of the product. The absorbent article includes an absorbent having a first surface which faces the body of a user and a second surface aligned opposite to the first surface. The absorbent has a pair of longitudinally extending arcuate sides which are arranged to be close to each other at a point approximate a central portion of the absorbent. A fluid permeable cover is positioned adjacent to at least the first surface of the absorbent and a fluid-impermeable baffle if positioned adjacent to at least the second surface of the absorbent. The cover and baffle are sealed together to enclose the absorbent. The seal is formed inward of the outer peripheral edge of the article. The article further includes a pair of elastic members affixed between the cover and the baffle outward of the seal and aligned adjacent to the central portion of the absorbent. The elastic members cause the absorbent article to acquire a cup-shaped configuration which corresponds to the perineal area of a user. The elastic members also bias a portion of the cover and baffle upward and outward to form walls adjacent to the central portion of the article which prevent side leakage of body fluids.

The general object of this invention is to provide an absorbent article having a cup-shaped configuration which better conforms to the curved shape of a human torso. A more specific object of this invention is to provide an absorbent article with upstanding side walls which prevent side leakage of body fluids deposited onto the cover of the product.

Another object of this invention is to provide a feminine care product with an hourglass shaped absorbent so that it is less prone to distortion during body movement.

A further object of this invention is to provide a sanitary napkin with an arcuate shape along its longitudinal axis to better fit the female body.

Still another object of this invention is to provide a feminine protection device which is relatively easy to manufacture and low in cost.

Still further, an object of this invention is to provide a sanitary napkin, pantiliner or incontinent garment with a curved profile which better conforms to the shape of a human body.

Other objects and advantages of the present invention will become more apparent to those skilled in the art in view of the following description and the accompanying drawings.

DETAILED DESCRIPTION OF THE PREFERRED EMBODIMENT

Figure 1:
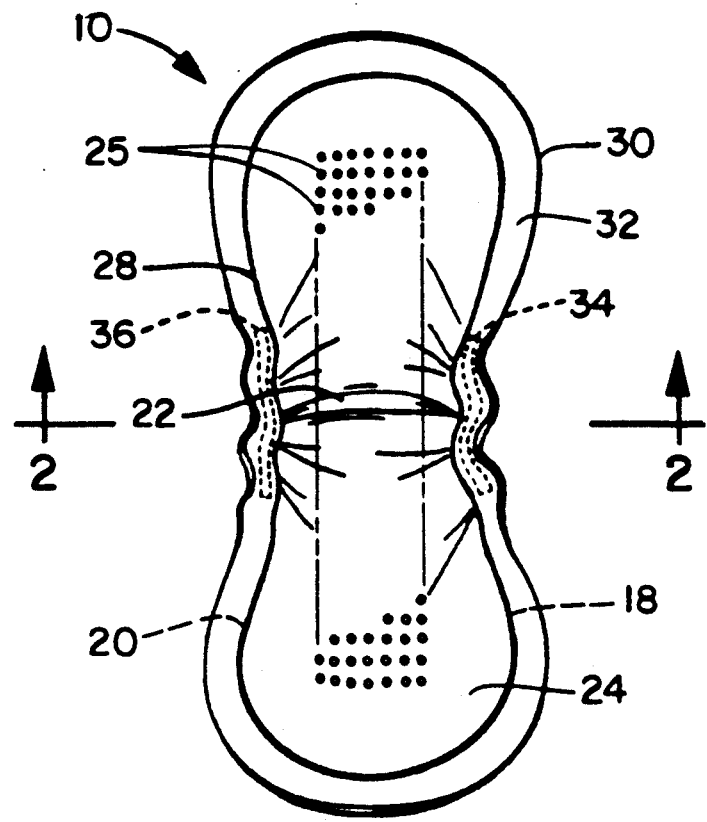
FIG. 1 is a plan view of an absorbent article having an hourglass shape with a pair of longitudinally extending arcuate sides which are arranged to be close to each other at a point approximate a central portion of the absorbent.
Figure 2:
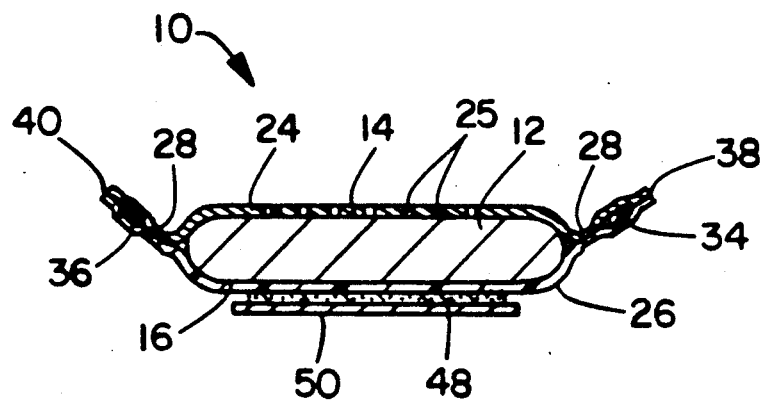
FIG. 2 is a cross-sectional view of the absorbent article shown in FIG. 1 taken along line 2—2.

Referring to FIGS. 1 and 2, an absorbent article 10 is shown in the shape of a feminine pad. It should also be noted that the absorbent article 10 can be a sanitary napkin, a pantiliner, a light incontinent garment, a feminine care pad, or other type of device designed to absorb body fluids such as blood, menses, urine, perspiration, etc. The absorbent article 10 preferably has an hourglass shape with a narrow central portion located between wider distal end portions. The absorbent 12 has a first surface 14 facing the body of a user and a second surface 16 aligned approximately opposite to the first surface 14. The absorbent 12 can have a uniform thickness or vary in thickness throughout its cross-section. Preferably, the absorbent 12 will be thicker in the middle and thinner at the distal ends. The absorbent 12 also has a pair of longitudinally extending arcuate sides 18 and 20. The arcuate sides 18 and 20 are aligned such that the closest point between them occurs at a central portion 22 of the absorbent 12. The absorbent 12 can be made out of a hydrophilic material such as cellulose fibers, wood pulp, regenerated cellulose or cotton fibers, or a blend of pulp and other fibers. Hydrocolloidal material, commonly referred to as superabsorbents, can also be added to the hydrophilic material to increase the absorption capacity.

A fluid permeable cover 24 is positioned adjacent to at least the first surface 14 of the absorbent 12. The cover 24 is designed to contact the body of the wearer and can be constructed of a woven or non-woven, natural or synthetic material which is easily penetrated by body fluids. Thermoplastic polymer webs made from fibers or filaments of polyethylene or polypropylene are preferred. It is also beneficial to form apertures 25 in the cover 24 to increase the rate at which body fluids can penetrate down into the absorbent 12.

A fluid-impermeable baffle 26 is positioned adjacent to at least the second surface 16 of the absorbent 12 and is sized and configured to be attached to the cover 24. The baffle 26 faces the inner surface, generally the crotch portion in the case of a feminine pad, of an undergarment (not shown). The baffle 26 will permit the passage of air or vapor out of the article 10 while blocking the passage of fluids or liquids. The baffle 26 can be made from polymeric films such as polyethylene, polypropylene or cellophane, or be made from a bicomponent film. A preferred material is ethyl-vinyl-acetate/-polyethylene coextruded film.

The cover 24 and the baffle 26 are sized and configured to be attached together to enclose the absorbent 12. Preferably, the cover 24 is sealed to the baffle 26 by a peripheral seal 28, best shown in FIG. 1. The seal 28 can be formed by the use of commercially available pressure-sensitive adhesives, by the use of heat and/or pressure, by the use of ultrasonics or by other known sealing means. The seal 28 will preferably extend continuously around the periphery of the absorbent 12 but it can also be discontinuous, if desired. The seal 28 is shown as being located inward from the peripheral edge 30 of the absorbent article 10 so as to form a fringe 32. The fringe 32 can have a width of between about 0.125-0-.750 inches, approximately 3.2-19.0 millimeters (mm). A preferred width is about 312 inches, approximately 7.9 mm. It should be noted that the fringe 32 can vary in width about the periphery of the absorbent article 10 although a uniform width is shown in the drawings. The fringe 32 creates a soft, pliable edge which is easily deformed by body movement since the cover 24 and the baffle 26 are not united over the width thereof. A soft fringe 32 is preferred for it adds comfort to the absorbent article 10 when worn between the thighs of a person.

The absorbent article 10 also contains a pair of elastic members 34 and 36 affixed between the cover 24 and the baffle 26 and located outward of the seal 28. The elastic members 34 and 36 are aligned adjacent to the central portion 22 of the absorbent 12 and have a width of between about 0.06-0.30 inches, approximately 1.5-7.6 mm. A preferred width is between about 0.15-0.20 inches, approximately 3.8-5.0 mm. Depending upon the size and shape of a particular product, the use of elastic members wider than about 0.30 inches, approximately 7.6 mm can cause problems due to the narrow width of the fringe 32. The use of wider elastic members could be uncomfortable if they come in contact with the thighs and cause chafing. The elastic members 34 and 36 should also be inset at least 0.06 inches, approximately 1.5 mm from the sides of the absorbent article 10. Preferably, the elastic members 34 and 36 are positioned midway between the seal line 28 and the outer peripheral edge 30 of the absorbent article 10 as is clearly shown in FIG. 1.

Figure 3:
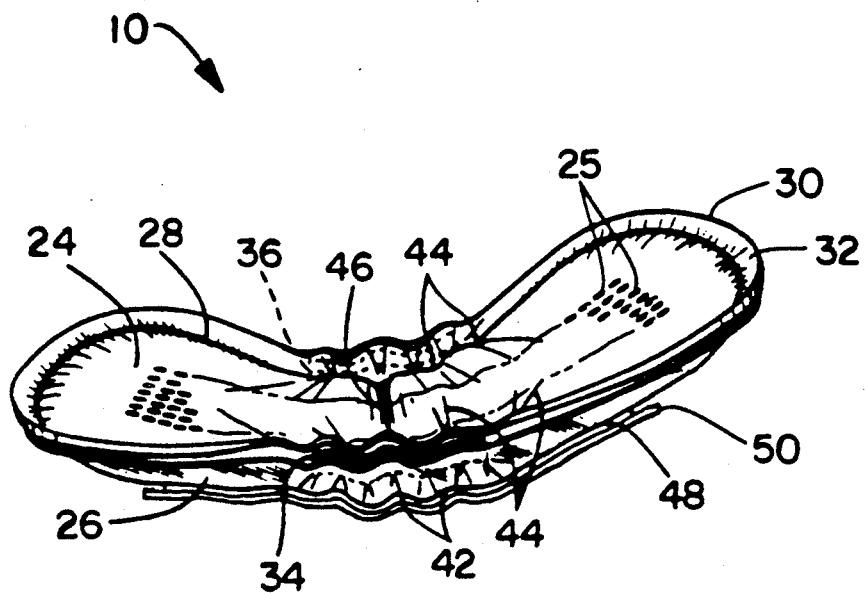
FIG. 3 is a side perspective view of the absorbent article shown in FIG. 1 partially turned toward the viewer and depicting the overall cup-shaped configuration.
Figure 4:
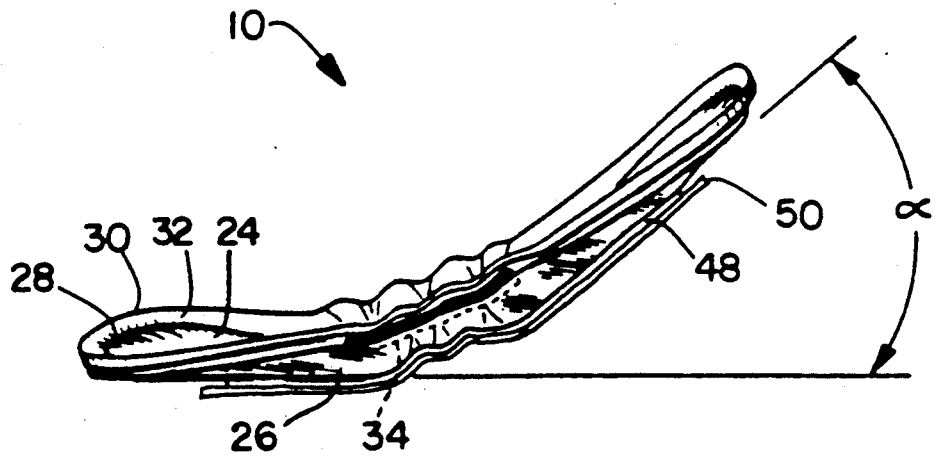
FIG. 4 is a side perspective view of the absorbent article shown in FIG. 1 with one end of the article resting on a horizontal plane to depict an angle alpha ($\alpha$) representing the amount of curvature in the cup-shaped article.

Referring to FIG. 3 and 4, the elastic members 34 and 36 cause the adjacent portions of the fringe 32 to acquire an upward and outward profile in the form of upstanding walls 38 and 40. The walls 38 and 40 assist in preventing side leakage of body fluids that may pool on the upper surface of the cover 24. The walls 38 and 40 will retain the body fluid on the top surface of the cover 24 until it can be absorbed down into the absorbent 12. The elastic members 34 and 36 also cause the absorbent article 10 to acquire a cup-shaped configuration which is best shown in FIG. 4. When the absorbent article 10 is positioned with one end resting on a horizontal plane, an angle alpha ($\alpha$) is formed by the outer profile of the edge of the article 10 with the horizontal plane. This angle is between about 30–90. The benefits associated with this cup-shaped configuration essentially disappear when the angle alpha ($\alpha$) is less than about 30°. It is also difficult to maintain the proper configuration of the absorbent article 10 should the angle alpha ($\alpha$) be greater than about 90°.

The elastic members 34 and 36 can be constructed out of any natural rubber or synthetic elastic including heat sealable and heat shrinkable materials. An example of a natural rubber elastic is L-1900 sold by Easthampton Rubber Company. Examples of heat sealable elastics include KRATON ™ 1107 sold by Shell Chemical Company and TUFTANE ™ TF-410 sold by B. F. Goodrich Company. Examples of heat shrinkable elastics include crystalline neoprene rubbers sold under the designation NEOPRENE ™ HC by E. I. du Pont de Nemours and Co, Inc. and polyurethane rubbers sold under the designation ESTANE ™ 5710 by B. F. Goodrich Company. Heat-shrinkable elastics may be easier to incorporate into certain manufacturing processes because the elastic can be applied in a non-elastic state, for example as a film, which becomes elastic upon the application of heat. The following U.S. Pat. Nos.: 3,639,917 issued to Althouse, 3,819,401 issued to Massengale et al. and 3,912,565 issued to Koch et al. teach various types of elastic materials applicable to absorbent articles as well as processes for attaching such elastic. These patents are incorporated by reference and made a part hereof. Another method of incorporating the elastic into the absorbent article 10 is by utilizing an elastic which can be extruded as a liquid and which upon cooling becomes an elastic adhesive. This method eliminates the need for a separate step of adhesively bonding strips of elastic to the cover 24 and/or to the baffle 26. An example of such an adhesive is taught in U.S. Pat. No. 4,259,220 issued to Bunnelle et al. which is incorporated by reference and made a part hereof.

The absorbent article 10 is essentially planar when the elastic members 34 and 36 are applied in a stretched condition and attached to either the cover 24, the baffle 26 or to both. The elastic members 34 and 36 distort the planar configuration of the absorbent article 10 when they return to their relaxed condition. This distortion pulls the ends of the absorbent article 10 upward toward each other and forces the central portion 22 to bow inward and produce a cup-shaped configuration. It has been found that at least one, and preferably both, of the elastic members 34 and 36 can have a length of about 10–70% of the overall length of the absorbent article 10. A more preferred length is between about 10–50% and a most preferred length is between about 10–30% of the overall length of the absorbent article 10. The use of shorter strips or bands of elastic will reduce the cost of the finished product. It should also be noted that the elastic members 34 and 36 can be individual strands or threads having a round, square or rectangular configuration or they can consist of two or more strands or threads united or grouped together to form a ribbon or band. The exact length of the elastic members 34 and 36 can vary depending upon: the degree of elasticity of each member, the stiffness and flexibility of the absorbent article 10, as well as other factors known to those skilled in the elastic art.

Experimental testing has shown that the best location for the elastic members 34 and 36 is to the outside of the seal 28. However, for certain products, it may be advantageous to position the elastic members 34 and 36 flush with or slightly to the inside of the seal 28.

When a self-adhering elastic is not employed, it may be necessary to provide another seal closer to the edge of the absorbent article 10 although this seal need not be continuous. The reason for the second seal would be to minimize the exposure to the edges of the cover 24 and the baffle 26 which also could cause chafing.

Referring again to FIGS. 3 and 4, one will notice that the absorbent article 10 is shown having a number of fold lines or constrictions 42 present along the central portion of the baffle 26 and corresponding fold lines or constrictions 44 present along the central portion of the cover 24 approximate the seal 28. A transverse fold line 46 is also present in the midsection of the absorbent article 10. The extent of the fold lines 42, 44 and 46 are dependent upon the width and length of the elastic members 34 and 36, the stiffness of the absorbent 12 and the stiffness of the absorbent article 10 as a whole. The degree of elasticity of the elastic members 34 and 36 is also relevant. These factors are balanced in order to produce an absorbent article 10 having an angle alpha ($\alpha$) between about 30°–90°. The presence of fold lines are not as detrimental in the cup-shape product as they would be in a relatively flat product because the walls 38 and 40 will retain any body fluids that may flow along these lines. It should be noted that the deepest part of the cup occurs at the central portion 22 of the absorbent article 10 and this deepest part is designed to be aligned with the perineal area of the woman when she wears the product. This unique arrangement assures that the body fluids will impinge upon the absorbent article 10 in the central portion 22. This is important because if pooling of the fluid should occur, the walls 38 and 40 will be adjacent to the pool of fluid and prevent side leakage.

The absorbent article 10 further contains a garment attachment adhesive 48 secured to the exterior surface of the baffle 26 and a removable peel strip 50. The peel strip 50, which can be a strip of paper, is designed to prevent foreign contaminates from contacting the adhesive 48. The peel strip 50 is designed to be removed just prior to use of the absorbent article 10 by the ultimate consumer. In use, the consumer removes the peel strip 50 and attaches the product, for example a sanitary napkin, to the inside surface of an undergarment so that the article 10 will remain in position relative to the perineum of the body.

While the invention has been described in conjunction with a specific embodiment, it is to be understood that many alternatives, modifications and variations will be apparent to those skilled in the art in light of the aforegoing description. Accordingly, this invention is intended to embrace all such alternatives, modifications and variations which fall within the spirit and scope of the appended claims.

I claim:

1. An absorbent article having an hour glass shape comprising:
   a) an absorbent having a first surface facing the body of a user and a second surface aligned approximately opposite to said first surface, said absorbent having a pair of longitudinally extending arcuate sides, said arcuate sides being closest to each other approximate a central portion of said absorbent;
   b) a fluid permeable cover positioned adjacent to at least said first surface of said absorbent;
   c) a fluid-impermeable baffle positioned adjacent to at least said second surface of said absorbent, said cover and baffle being sealed together to enclose said absorbent, said seal being formed inward of the outer peripheral edge of said hour-glass-shaped article; and
   d) a pair of elastic members affixed between said cover and said baffle outward of said seal and aligned adjacent to said central portion of said absorbent, said elastic members causing said article to acquire a cup-shaped configuration with said central portion forming the deepest portion of said cup which corresponds to the perineal area of a user.

2. The absorbent article of claim 1 wherein said cup-shaped configuration produces an angle formed by the outer profile of the edge of said article and a plane upon which said article rests of between about 30°-90°.

3. The absorbent article of claim 1 wherein said seal extends continuously around the periphery of said absorbent.

4. The absorbent article of claim 1 wherein at least one of said elastic members has a length of between about 10-70% of the overall length of said article.

5. The absorbent article of claim 4 wherein each of said elastic members have a length of between about 10-70% of the overall length of said article.

6. The absorbent article of claim 5 wherein each of said elastic members have a length of between about 10-50% of the overall length of said article.

7. The absorbent article of claim 6 wherein each of said elastic members have a length of between about 10-30% of the overall length of said article.

8. A sanitary napkin having an hour-glass shape comprising:
   a) an hourglass shaped absorbent having a first surface facing the body of a user and a second surface aligned approximately opposite to said first surface, said absorbent having a pair of longitudinally extending arcuate sides, said arcuate sides being closest to each other approximate a central portion of said absorbent;
   b) a fluid permeable cover positioned adjacent to at least said first surface of said absorbent;
   c) a fluid-impermeable baffle positioned adjacent to at least said second surface of said absorbent, said cover and baffle being sealed together to enclose said absorbent, said seal being formed inward of the outer peripheral edge of said hour-glass-shaped napkin; and
   d) a pair of elastic members affixed between said cover and said baffle and positioned adjacent to said central portion inbetween said seal and the outer periphery of said napkin, said elastic members causing said napkin to acquire a cup-shaped configuration with said central portion forming the deepest portion of said cup which corresponds to the perineal area of a user.

9. The sanitary napkin of claim 8 wherein said cup-shaped configuration produces an angle formed by the outer profile of the edge of said napkin and a plane upon which said napkin rests of between about 30°-90°.

10. The sanitary napkin of claim 8 wherein each of said elastic members are affixed on opposite sides of said absorbent at an equal distance between said seal and the outer peripheral edge of said sanitary napkin.

11. The sanitary napkin of claim 8 wherein at least one of said elastic members has a length of between about 10-70% of the overall length of said napkin.

12. The sanitary napkin of claim 11 wherein each of said elastic members have a length of between about 10-70% of the overall length of said napkin.

13. The sanitary napkin of claim 12 wherein each of said elastic members have a length of between about 10-50% of the overall length of said napkin.

14. The sanitary napkin of claim 13 wherein each of said elastic members have a length of between about 10-30% of the overall length of said napkin.

15. The sanitary napkin of claim 8 wherein said cover is sealed to said baffle by an adhesive.

16. A sanitary napkin having an hour-glass shape comprising:
   a) an absorbent having a first surface facing the body of a user and a second surface aligned approximately opposite to said first surface, said absorbent having a pair of longitudinally extending arcuate sides, said arcuate sides being closest to each other approximate a central portion of said absorbent;
   b) a fluid permeable cover positioned adjacent to at least said first surface of said absorbent;
   c) a fluid-impermeable baffle positioned adjacent to at least said second surface of said absorbent, said cover and baffle being sealed together to enclose said absorbent, said seal being formed inward of the outer peripheral edge of said hour-glass-shaped napkin; and
   d) a pair of elastic members affixed between said cover and said baffle outward of said seal and aligned adjacent to said central portion of said absorbent, said elastic members having a length of between about 10-70% of the overall length of said napkin, said elastic members causing said napkin to acquire a cup-shaped configuration which produces an angle formed by the outer profile of the edge of said napkin and a plane upon which said napkin rests of between about 30°-90°, and said central portion forming the deepest portion of said cup which corresponds to the perineal area of a user.

17. The sanitary napkin of claim 16 wherein said absorbent has an hourglass shape with a narrow central portion located between wider distal end portions.

* * * * *

UNITED STATES PATENT AND TRADEMARK OFFICE
CERTIFICATE OF CORRECTION

PATENT NO. : 5,032,121

DATED : July 16, 1991

INVENTOR(S) : Patti J. Mokry

It is certified that error appears in the above-identified patent and that said Letters Patent is hereby corrected as shown below:

In Column 2, Line 35, delete the word "fluid" and substitute therefor --fluids--.

In Column 2, Line 61, delete the word "adJacent" and substitute therefor --adjacent--.

In Column 4, Line 40, delete the word "312" and substitute therefor --.312--.

In Column 5, Line 17, delete the words "30-90" and substitute therefor --30°-90°--.

Signed and Sealed this

Fourteenth Day of December, 1993

*Attest:*

BRUCE LEHMAN

*Attesting Officer*  *Commissioner of Patents and Trademarks*